_(12)_ United States Patent
Takagi et al.

(10) Patent No.: US 8,148,134 B2
(45) Date of Patent: Apr. 3, 2012

(54) MICROORGANISM CAPABLE OF DEGRADING DIPHENYLARSINIC ACID

(75) Inventors: Kazuhiro Takagi, Tsukuba (JP); Naoki Harada, Tsukuba (JP)

(73) Assignee: Kowa Company, Ltd., Nagoya-shi (JP)

( * ) Notice: Subject to any disclaimer, the term of this patent is extended or adjusted under 35 U.S.C. 154(b) by 238 days.

(21) Appl. No.: 12/439,662

(22) PCT Filed: Aug. 24, 2007

(86) PCT No.: PCT/JP2007/000907

§ 371 (c)(1),
(2), (4) Date: Mar. 2, 2009

(87) PCT Pub. No.: WO2008/026309

PCT Pub. Date: Mar. 6, 2008

(65) Prior Publication Data

US 2010/0015688 A1      Jan. 21, 2010

(30) Foreign Application Priority Data

Sep. 1, 2006   (JP) .................. 2006-238350
Apr. 25, 2007  (JP) .................. 2007-115920

(51) Int. Cl.
*C12N 1/12*     (2006.01)
*C12F 3/34*     (2006.01)
(52) U.S. Cl. ................... 435/252.1; 435/262
(58) Field of Classification Search .......... None
See application file for complete search history.

(56) References Cited

OTHER PUBLICATIONS

Nakamiya et al. Degradation of arylarsenic compounds by microorganisms, FEMS Microbiol Lett 274, 184-188, E. pub Jun. 30, 2007.*
Lynch et al. J Bacteriol. May 2004;186(10):2996-3005.*
Yang et al. J Bacteriol. 2005;187(20):6991-6997.*
Lynch et al. J Bacteriol. Apr. 2001; 183(8):2576-85.*
International Search Report of PCT/JP2007/000907, Mailing Date of Nov. 13, 2007.
K. Nakamiya et al., "Jifeniruhisan no Biseibutus Bunkai", Nippon Seibutsu Kogakukai Taikai Koen Yoshishu, 2005, vol. 2005, p. 95, (3B13-4); Cited in ISR.
A. Noguchi et al., "Dojo Biseibutsu ni yoru Diphenylarsinic Acid no Bunkai Oyobi Dojochu Diphenylarsinic Acid, Phenylarsonic Acid no Kenshutsuho no Kento", Symposium on Environmental Chemistry Program and Abstracts, 2005, vol. 14, pp. 224-225, (2C-1); Cited in ISR.
N. Harada et al., "Diphenylarsinic Acid Bunkaikin Sinorhizobium sp.L2406 Kabu ni yoru Yuki Hiso Kagobutsu no Mukika", Abstracts of the Annual Meeting, Japanese Society of Soil Science and Plant Nutrition, Aug. 22, 2007, vol. 53, p. 42, (6-21); Cited in ISR.
N. Harada et al., "Suiden Dojo kara no Diphenylarsinic Acid Bunkaikin Tanri no Kokoromi", Abstracts of the Annual Meeting, Japanese Society of Soil Science and Plant Nutrition, Sep. 5, 2006, vol. 52, p. 36, (P6-3); Cited in ISR.
Supplementary European Search Report dated Sep. 20, 2010, issued in corresponding European Patent Application No. 07805773.4.
Harada, Naoki et al.; "Biodegradation of diphenylarsinic acid to arsenic acid by novel soil bacteria isolated from contaminated soil"; Biodegration, vol. 21, No. 3, Jun. 2010, pp. 491-499, XP002599455.

* cited by examiner

*Primary Examiner* — Anand Desai
*Assistant Examiner* — Iqbal H Chowdhury
(74) *Attorney, Agent, or Firm* — Westerman, Hattori, Daniels & Adrian, LLP

(57) ABSTRACT

Disclosed are: a microorganism capable of degrading diphenylarsinic acid; a method for degrading diphenylarsinic acid by using the microorganism; a method for clean-up of a contaminated soil by using the microorganism; an agent for degrading diphenylarsinic acid, which comprises the microorganism; and a cleaning agent for a contaminated soil or groundwater, which comprises the microorganism. Specifically disclosed are: a microorganism belonging to the genus *Sinorhizobium* and capable of degrading diphenylarsinic acid; a microorganism belonging to the genus *Ensifer* and capable of degrading diphenylarsinic acid; a method for clean-up of a contaminated soil by using the microorganism; an agent for degrading diphenylarsinic acid, which comprises the microorganism; and a cleaning agent for a contaminated soil or groundwater, which comprises the microorganism.

15 Claims, 3 Drawing Sheets

[FIG.1]
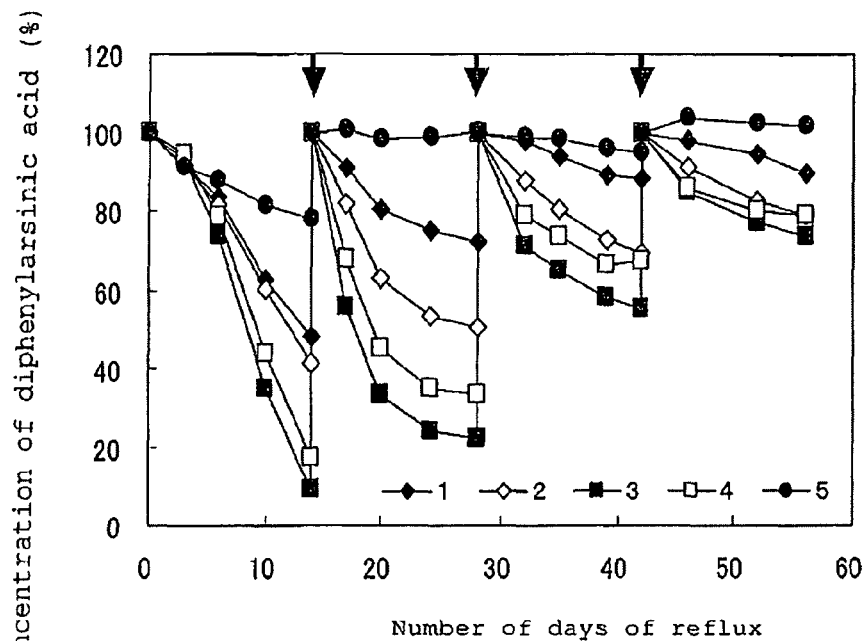
(Remarks) The ordinate indicates the relative values with respect to the initial diphenylarsinic acid concentration, while the arrows indicate the time points of replacement of the reflux liquid.
[FIG.2]
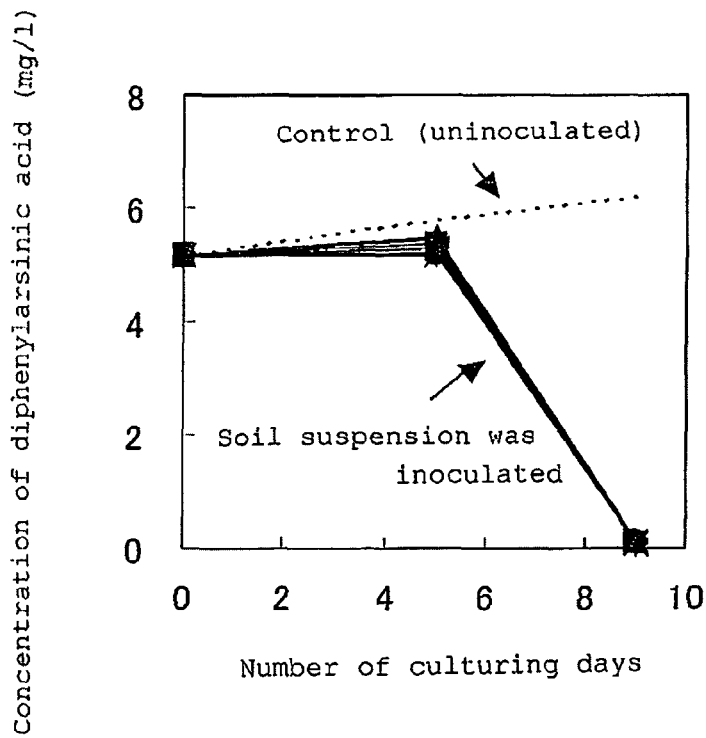

[FIG.3]
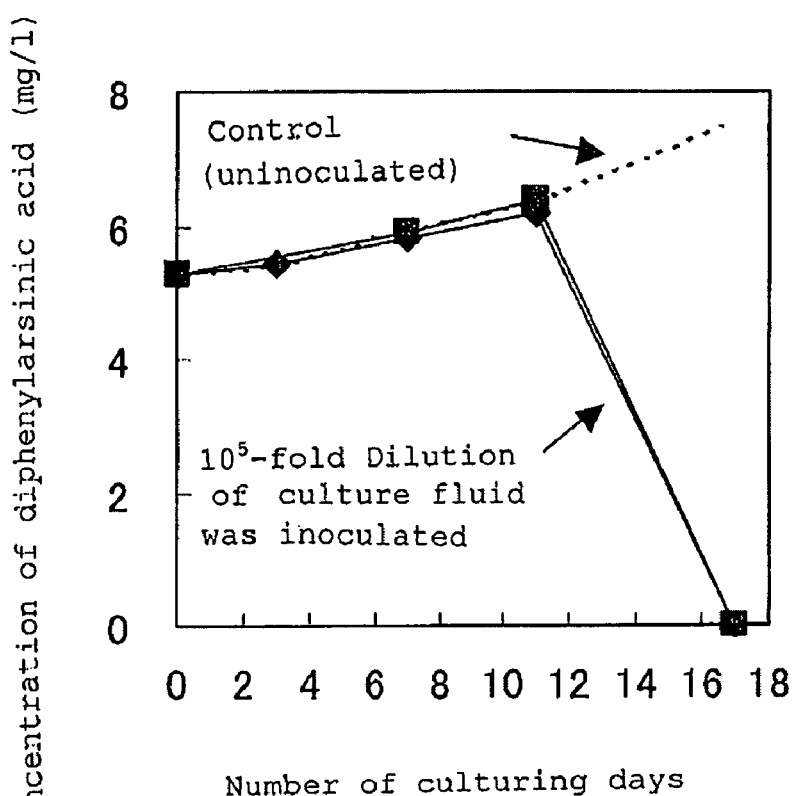
[FIG.4]
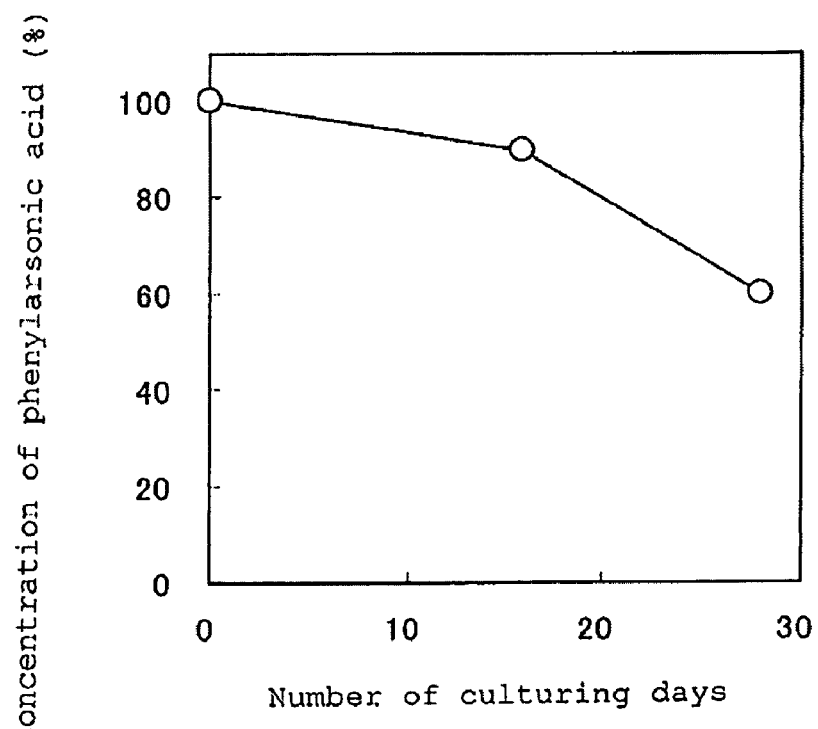

[FIG.5]
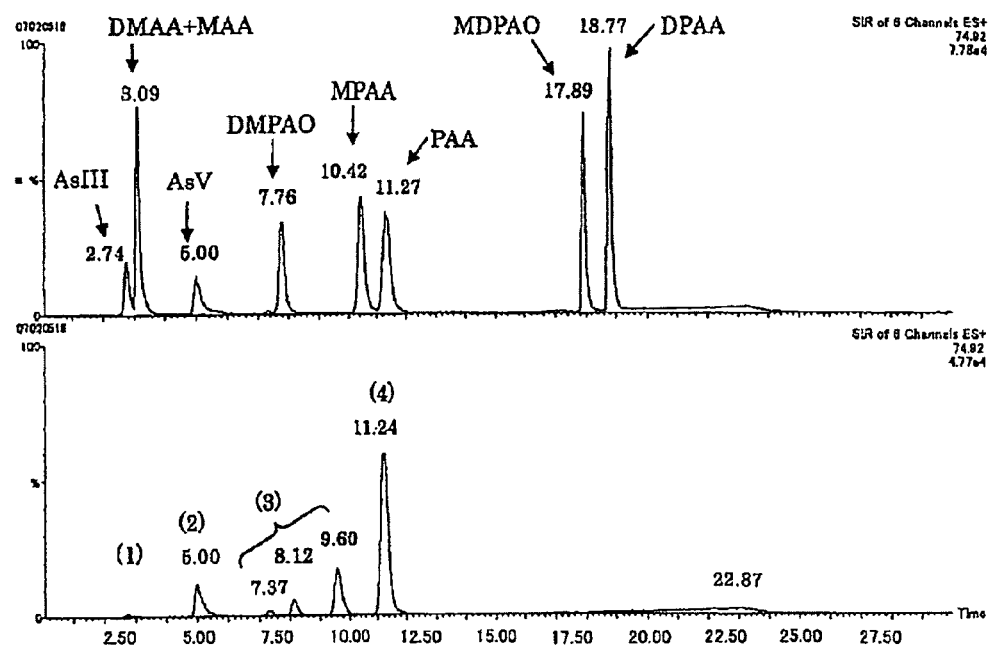
[FIG.6]
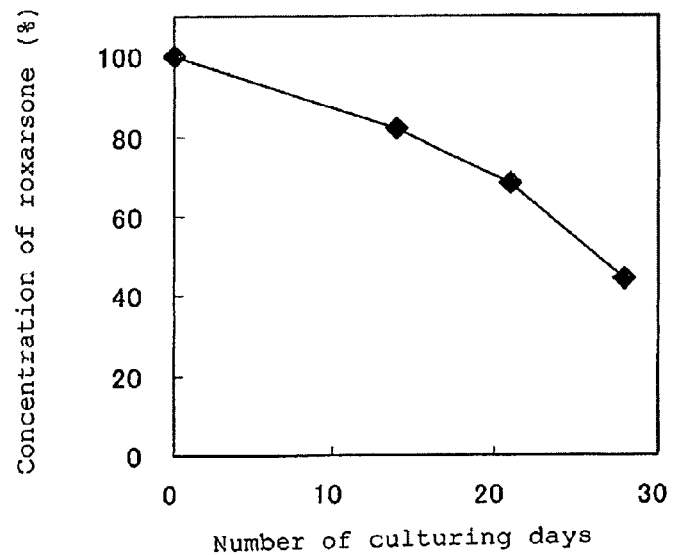

SEQUENCE LISTING

<160> NUMBER OF SEQ ID NOS: 4

<210> SEQ ID NO 1
<211> LENGTH: 1101
<212> TYPE: DNA
<213> ORGANISM: Sinorhizobium sp. L2406

<400> SEQUENCE: 1

```
tggggaatat tggacaatgg gcgcaagcct gatccagcca tgccgcgtga gtgatgaagg     60
ccctagggtt gtaaagctct tcaccggtg aagataatga cggtaaccgg agaagaagcc    120
ccggctaact tcgtgccagc agccgcggta atacgaaggg gctagcgtt gttcggaatt    180
actgggcgta aagcgcacgt aggcggacat ttaagtcagg ggtgaaatcc cagagctcaa    240
ctctggaact gcctttgata ctgggtgtct agagtatgga agaggtgagt ggaattccga    300
gtgtagaggt gaaattcgta gatattcgga ggaacaccag tggcgaaggc ggctcactgg    360
tccattactg acgctgaggt gcgaaagcgt ggggagcaaa caggattaga taccctggta    420
gtccacgccg taacgatga atgttagccg tcgggcagtt tactgttcgg tggcgcacgt    480
aacgcattaa acattccgcc tggggagtac ggtcgcaaga ttaaaactca aaggaattga    540
cgggggccgc acaagcggtg gagcatgtgg tttaattcga agcaacgcgc agaaccttac    600
cagcccttga catcccgatc gcggattaca gagatgtagt ccttcagttc ggctggatcg    660
gagacaggtg ctgcatggct gtcgtcagct cgtgtcgtga gatgttgggt taagtcccgc    720
aacgagcgca accctcgccc ttagttgcca gcattaagtt gggcactcta aggggactgc    780
cggtgataag ccgagaggaa ggtggggatg acgtcaagtc ctcatggccc ttacgggctg    840
ggctacacac gtgctacaat ggtggtgaca gtgggcagcg agaccgcgag gtcgagctaa    900
tctccaaaag ccatctcagt tcggattgca ctctgcaact cgagtgcatg aagttggaat    960
cgctagtaat cgcagatcag catgctgcgg tgaatacgtt cccgggcctt gtacacaccg   1020
cccgtcacac catgggagtt ggttctaccc gaaggtagtg cgctaaccgc aaggaggcag   1080
ctaaccacgg tagggtcagc g                                             1101
```

<210> SEQ ID NO 2
<211> LENGTH: 1276
<212> TYPE: DNA
<213> ORGANISM: Ensifer sp. L2413

<400> SEQUENCE: 2

```
taccgtatga gcccttcggg ggaaagattt atcgggaaag gatgagcccg cgttggatta     60
gctagttggt ggggtaaagg cctaccaagg cgacgatcca gctggtct gagaggatga    120
tcagccacat tgggactgag acacggccca aactctacgg gaggcagcag tgggaatat    180
tggacaatgg gcgcaagctg atccagccat gccgcgtgag tgatgaaggc cctaggtttg    240
taaagctctt tcaccggtga agataatgac ggtaaccgga gaagaagccc cggctaactt    300
cgtgccagca gccgcggtaa tacgaagggg ctagcgttg ttcggaatta ctgggcgtaa    360
agcgcacgta ggcggacatt taagtcaggg gtgaaatccc ggggctcaac cccggaactg    420
cctttgatac tgggtgtcta gagtatggaa gaggtgagtg gaattccgag tgtagaggtg    480
```

```
aaattcgtag atattcggag gaacaccagt ggcgaaggcg gctcactggt ccattactga      540
cgctgaggtg cgaaagcgtg gggagcaaac aggattagat accctggtag tccacgccgt      600
aaacgatgaa tgttagccgt cgggcagttt actgttcggt ggcgcacgta acgcattaaa      660
cattccgcct ggggagtacg gtcgcaagat taaaactcaa aggaattgac ggggccgca       720 caagcggtgg agcatgtggt ttaattcgaa gcaacgcgca gaaccttacc agcccttgac      780
atcccgatcg cggattacgg agacgttttc cttcagttcg gctggatcgg agacaggtgc      840
tgcatggctg tcgtcagctc gtgtcgtgag atgttgggtt aagtcccgca acgagcgcaa      900
ccctcgccct tagttgccag catttagttg ggcactctaa ggggactgcc ggtgataagc      960
cgagaggaag gtggggatga cgtcaagtcc tcatggccct tacgggctgg gctacacacg     1020
tgctacaatg gtggtgacag tgggcagcga gaccgcgagg tcgagctaat ctccaaaagc     1080
catctcagtt cggattgcac tctgcaactc gagtgcatga agttggaatc gctagtaatc     1140
gcagatcagc atgctgcggt gaatacgttc ccgggccttg tacacaccgc ccgtcacacc     1200
atgggagttg gttctacccg aaggtagtgc gctaaccgca aggaggcagc taaccacggt     1260
agggtcagcg actggg                                                    1276

<210> SEQ ID NO 3
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 3
agagtttgat cctggctcag                                                   20

<210> SEQ ID NO 4
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 4
aaggaggtga tccagcc                                                      17
```

MICROORGANISM CAPABLE OF DEGRADING DIPHENYLARSINIC ACID

TECHNICAL FIELD

The present invention relates to a microorganism which belongs to genus *Sinorhizobium* and has an ability to degrade diphenylarsinic acid. The present invention also relates to a microorganism which belongs to genus *Ensifer* and has an ability to degrade diphenylarsinic acid. Furthermore, the invention relates to a method for degrading diphenylarsinic acid by using at least one or more of the microorganisms.

BACKGROUND ART

In March 2003, arsenic was detected from the drinking water from wells in Kamisu city, Ibaraki Prefecture, at a concentration as high as 450-fold the water quality standard. Investigations made thereafter revealed that this arsenic originated from one species of organoarsenic compound, specifically, a phenylated arsenic compound containing diphenylarsinic acid $[(C_6H_5)_2AsO(OH)$; the structural formula is shown as formula (I)] as a main component.

Formula I:

[Chemical Formula 1]

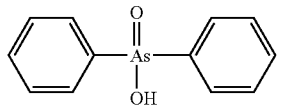

Contamination by this phenylated arsenic compound directly resulted in damages to the health of neighboring residents, and incorporation of arsenic into the rice produced in the vicinal paddy fields was also detected. The arsenic contamination of the soil or underground water in this area, which has been caused by diphenylarsinic acid, seems to be still in progress to a large extent, and thus investigations involving monitoring by the Ministry of the Environment of Japan are being continuously carried out to the present.

Diphenylarsinic acid is a raw material for the synthesis of diphenylcyanoarsine or diphenylchloroarsine, which are both used as emetics (sternutators), which belong to a kind of chemical weapons, and diphenylarsinic acid is also a hydrolysis product. When diphenylcyanoarsine or diphenylchloroarsine is dumped into the soil, the compounds undergo conversion to diphenylarsine hydroxide and bis(diphenylarsine) oxide, and are finally converted to diphenylarsinic acid. In Japan, the soil contamination which is believed to be caused by abandonment of chemical weapons including these organoarsenic compounds, is being discovered at the sites where military installations constructed 60 or more years ago used to be present, or the neighborhood. Also, in abroad countries, organoarsenic contamination of soil or underground water which is believed to be caused by the dumping of chemical weapons, is being confirmed. However, technologies for the restoration of such organoarsenic-contaminated soil are yet to be established.

As a conventional method for purifying soils contaminated with organoarsenic compounds, a method of extracting and removing organoarsenic compounds from the contaminated soil by washing treatments has been proposed (Patent Document 1). In that case, any of an aqueous solution containing sodium hydroxide, an aqueous solution containing phosphoric acid or a salt thereof, an aqueous solution containing sulfuric acid, an aqueous solution containing hydrochloric acid, an aqueous solution containing tartaric acid or a salt thereof, an aqueous solution containing citric acid or a salt thereof, and an aqueous solution containing oxalic acid or a salt thereof, is used as the washing agent.

As a method for purifying organoarsenic compound-containing water, there has been a proposed method of treating an organoarsenic compound by reacting the organoarsenic compound with hydrogen peroxide in the presence of at least one metal ion selected from the group consisting of iron ions, copper ions, cobalt ions and manganese ions, to thereby oxidatively degrading the organoarsenic compound to inorganic arsenic (Patent Document 2). Alternatively, there has been a proposed method of reducing an organoarsenic compound by adding an inorganic flocculant such as ferric chloride and an organic polymer flocculant to form flocs, precipitating and separating these flocs, subsequently filtering the precipitation treatment water through a sand filter, and then further subjecting the treated water to adsorption with activated carbon (Patent Document 3). There has also been a proposed method characterized by degrading an organoarsenic compound to an inorganic arsenic compound by blowing ozone gas while irradiating the organoarsenic compound-containing water with ultraviolet radiation (Patent Document 4).

Furthermore, there have been a proposed water treatment method characterized in that a precipitation process of adding a flocculant to water containing organic arsenic to precipitate and remove the contained organic arsenic is carried out, followed by a reverse osmosis membrane process of removing any organic arsenic remaining in the water by means of a reverse osmosis membrane; and a water treatment apparatus including a reverse osmosis membrane apparatus for treating a water containing organic arsenic, the water treatment apparatus being characterized by having a precipitation tank for precipitating the organic arsenic by mixing a flocculant to the water, which is disposed upstream to the reverse osmosis membrane apparatus (Patent Document 5).

However, in the case of applying the above-described method for purifying organoarsenic compounds to any contaminated soil, it is necessary to perform excavation of contaminated soil or water abstraction, extraction of organic arsenic, and the like, and thus enormous efforts and costs are required. Therefore, a method which is more convenient and capable of in situ purification is desired, and as one of the new environment purifying technologies appropriate for such requirements, bioremediation is attracting the public attention. For the implementation of the technology, a microorganism capable of effectively degrading and removing the subject contaminant is indispensable, but in the case of applying this technique to the environmental contamination involving organoarsenic compounds, there is a problem that no useful microorganism has been isolated.

To date, as for the microorganisms degrading organoarsenic compounds, strain K8, strain 12M17 and strain 7M5 have been reported as microorganisms capable of degrading dimethylarsinic acid, and strain K-1' and strain IV-1 have been reported as microorganisms capable of degrading monomethylarsonic acid (Patent Document 6). The strain K-1' and strain IV-1 are reported to be capable of degrading phenylarsonic acid as well, albeit only slightly (Patent Document 6). However, there is no bacterium known hitherto as degrading diphenylarsinic acid, which is an organoarsenic compound detected in highest concentrations with regard to the arsenic contamination in Kamisu city as mentioned above.

The disclosures of Patent Document 1 (Japanese Patent Application Laid-Open (JP-A) No. 2005-169162), Patent Document 2 (JP-A No. 2001-158622), Patent Document 3 (JP-A No. 2005-238184), Patent Document 4 (JP-A No. 2005-334761), Patent Document 5 (JP-A No. 2006-43616) and Patent Document 6 (JP-A No. 2005-229945) are incorporated as part of the description of the present specification.

Patent Document 1: JP-A No. 2005-169162
Patent Document 2: JP-A No. 2001-158622
Patent Document 3: JP-A No. 2005-238184
Patent Document 4: JP-A No. 2005-334761
Patent Document 5: JP-A No. 2006-43616
Patent Document 6: JP-A No. 2005-229945

DISCLOSURE OF THE INVENTION

Problems to be Solved by the Invention

Diphenylarsinic acid is a kind of organoarsenic compound, and causes contamination of soil or underground water through the dumping of diphenylarsinic acid itself, or through the hydrolysis of chemical weapons (diphenylcyanoarsine or diphenylchloroarsine) abandoned in the soil. As a means to improve such circumstances, a means for efficiently degrading diphenylarsinic acid is being desired.

Therefore, it is an object of the present invention to provide microorganisms having an ability to degrade diphenylarsinic acid, a method for degrading diphenylarsinic acid by using the microorganism, a method of purifying contaminated soil and/or underground water by using the microorganism, a degradation agent of diphenylarsinic acid including the microorganism, and a purifying agent for contaminated soil and/or contaminated underground water, which agent includes the microorganism.

Means for Solving the Problems

In order to solve the above-described problems, the inventors of the present invention carried out enrichment culture, and found that there are microorganisms effective for this purpose in the paddy field soil which has been contaminated with diphenylarsinic acid. The inventors further found that a novel bacterium of genus *Ensifer* and a novel bacterium of genus *Sinorhizobium*, which have been isolated among those above-mentioned microorganisms, have high ability of degrading diphenylarsinic acid. The inventors also found that degradation of diphenylarsinic acid by the microorganisms is accelerated by the addition of an iron component such as ferrous sulfate, and thus completed the present invention.

The present invention provides the following inventions of [1] to [13].

[1] A microorganism having an ability to degrade diphenylarsinic acid and belonging to genus *Sinorhizobium*.

[2] A microorganism having an ability to degrade diphenylarsinic acid and belonging to genus *Sinorhizobium*, the microorganism having a 16S ribosomal RNA gene containing the following (A) or (B):
  (A) a DNA having the base sequence set forth in SEQ ID NO:1, or
  (B) a DNA having an identity of 95% or more with the base sequence set forth in SEQ ID NO:1.

[3] Strain L2406 (FERM BP-10658) having an ability to degrade diphenylarsinic acid and belonging to genus *Sinorhizobium*.

[4] A microorganism having an ability to degrade diphenylarsinic acid and belonging to genus *Ensifer*.

[5] A microorganism having an ability to degrade diphenylarsinic acid and belonging to genus *Ensifer*, the microorganism having a 16S ribosomal RNA gene containing the following (A) or (B):
  (A) a DNA having the base sequence set forth in SEQ ID NO:2, or
  (B) a DNA having an identity of 95% or more with the base sequence set forth in SEQ ID NO:2.

[6] Strain L2413 (FERM BP-10659) having an ability to degrade diphenylarsinic acid and belonging to genus *Ensifer*.

[7] A method for degrading diphenylarsinic acid by using the microorganism according to any one of [1] to [6].

[8] A method of purifying soil and/or contaminated underground water by using the microorganism according to any one of [1] to [6].

[9] The method according to [7] or [8], wherein the microorganism is used in the presence of an iron component.

[10] A degradation agent of diphenylarsinic acid, the degradation agent including the microorganism according to any one of [1] to [6].

[11] The degradation agent according to [10], including an iron component.

[12] A purifying agent for contaminated soil and/or contaminated underground water, the purifying agent including the microorganism according to any one of [1] to [6].

[13] The purifying agent according to [12], including an iron component.

The present invention also relates to the following [14] to [18].

[14] A method for producing phenyl arsonic acid by degrading diphenylarsinic acid using the microorganism according to any one of [1] to [6].

[15] A method for producing purified soil from contaminated soil by using the microorganism according to any one of [1] to [6].

[16] A method for producing purified underground water from contaminated underground water, by using the microorganism according to any one of [1] to [6].

[17] The method according to anyone of [14] to [16], wherein the microorganism is used in the presence of an iron component.

[18] A method for screening a bacterial strain having an ability to degrade diphenylarsinic acid, the method including:
  collecting arsenic-contaminated soil while still wet;
  culturing the arsenic-contaminated soil in the presence of diphenylarsinic acid to obtain a culture fluid;
  diluting the obtained culture fluid to prepare a dilution series;
  culturing the culture fluids of the dilution series in the presence of diphenylarsinic acid; and
  selecting, among the dilution series, a culture fluid exhibiting a reduction of concentration or disappearance of diphenylarsinic acid concomitantly with the culturing.

That is, the present invention first provides a microorganism which has an ability to degrade diphenylarsinic acid and belongs to genus *Sinorhizobium*. As such a microorganism, a microorganism having an ability to degrade diphenylarsinic acid and belonging to genus *Sinorhizobium*, which microorganism has a 16S ribosomal RNA gene containing the following (A) or (B) is preferred:
  (A) a DNA having the base sequence set forth in SEQ ID NO:1, or
  (B) a DNA having an identity of 95% or more with the base sequence set forth in SEQ ID NO:1.

The aforementioned identity is preferably 95% or more, more preferably 96% or more, even more preferably 97% or more, still more preferably 98% or more, and still more preferably 99% or more, and it is preferable that the identity be particularly 99.5% or more, particularly 99.8% or more, and particularly 99.9% or more. As such a microorganism, strain L2406 (FERM BP-10658) belonging to genus *Sinorhizobium* is highly preferable.

Furthermore, the present invention provides a microorganism which has an ability to degrade diphenylarsinic acid and belongs to genus *Ensifer*. As such a microorganism, a microorganism having an ability to degrade diphenylarsinic acid and belonging to genus *Ensifer*, which microorganism has a 16S ribosomal RNA gene containing the following (A) or (B) is preferred:

(A) a DNA having the base sequence set forth in SEQ ID NO: 2, or (B) a DNA having an identity of 95% or more with the base sequence set forth in SEQ ID NO: 2.

The aforementioned identity is preferably 95% or more, more preferably 96% or more, even more preferably 97% or more, still more preferably 98% or more, and still more preferably 99% or more, and it is preferable that the identity be particularly 99.5% or more, particularly 99.8% or more, and particularly 99.9% or more. As such a microorganism, strain L2413 (FERM BP-10659) belonging to genus *Ensifer* is highly preferable.

The present invention also provides a method for degrading diphenylarsinic acid by using at least one or more of the above-mentioned microorganisms; a method for producing phenylarsonic acid by degrading diphenylarsinic acid; a method of purifying contaminated soil and/or contaminated underground water; a method for producing purified soil from contaminated soil; and a method for producing purified contaminated underground water from contaminated underground water, and the invention also provides the use of the above-mentioned microorganisms for these methods. Furthermore, in preferred embodiments of these methods and use, the methods and the use may be implemented in the presence of an iron component. The amount of the iron component incorporated to be used together with the microorganisms is, in terms of iron concentration [mg-Fe/l] (mass of iron, mg, per liter of the volume), generally 0.01 [mg-Fe/l] or more, preferably 0.04 [mg-Fe/l] or more, more preferably 0.1 [mg-Fe/l] or more, even more preferably 0.2 [mg-Fe/l] or more, still more preferably 0.3 [mg-Fe/l] or more, still more preferably 0.4 [mg-Fe/l] or more, even more preferably 1 [mg-Fe/l] or more, still more preferably 2 [mg-Fe/l] or more, and even more preferably 4 [mg-Fe/l] or more. Thus, a higher iron concentration tends to be more preferable. The upper limit of the iron concentration is not particularly limited, and may be set to the saturation concentration which is determined by the ionic product, but the upper limit is in general 1000 [mg-Fe/l] or less. These iron concentrations can be achieved by the addition of, for example, an iron component such as ferrous sulfate.

The term contaminated soil or underground water refers to arsenic-contaminated soil or underground water, with the arsenic mainly including diphenylarsinic acid. The term arsenic-contaminated soil or underground water refers to a soil or underground water contaminated by generally containing the arsenic element in the form of organic compounds and inorganic compounds, but according to the present invention, the term refers to arsenic-contaminated soil or underground water, with the arsenic mainly including diphenylarsinic acid. Purification of contaminated soil or contaminated underground water refers to the obtainment of soil or underground water, with mainly diphenyl arsenic acid having been removed. However, such purification of contaminated soil or purification of contaminated underground water encompasses that organoarsenic compounds which serve as the source of generation of diphenylarsinic acid, are rapidly removed from soil or underground water as a result of adequately removing diphenylarsinic acid, and also encompasses that general organoarsenic compounds are rapidly removed from soil or underground water by using known compositions and methods for accelerating the degradation of phenylarsonic acid, in combination.

The present invention also provides a degradation agent of diphenylarsinic acid and a purifying agent for contaminated soil or contaminated underground water, both of the agents including the above-mentioned microorganisms, and also provides a method of using the above-mentioned microorganisms for the production of these agents. These degradation agent, soil purifying agent and underground water purifying agent include the above-mentioned microorganisms as an active ingredient, and can also include known auxiliary components which are acceptable for the purpose. Furthermore, in a preferred embodiment, these degradation agent, soil purifying agent and underground water purifying agent can include an iron component such as ferrous sulfate. A suitable content of the iron component is preferably set such that the amount of the iron component present when used together with the microorganisms against soil, underground water and the like in the degradation or purification, would have a value in the above-described range, in terms of the iron concentration [mg-Fe/l] (mass of iron, mg, per liter of the volume).

Furthermore, the present invention also resides in a method for selecting (screening) a strain of microorganism having an ability to degrade diphenylarsinic acid, the method including the following steps:

collecting arsenic-contaminated soil while still wet;

culturing the arsenic-contaminated soil in the presence of diphenylarsinic acid to obtain a culture fluid;

diluting the obtained culture fluid to prepare a dilution series;

culturing the culture fluids of the dilution series in the presence of diphenylarsinic acid; and selecting, among the dilution series, a culture fluid exhibiting a reduction of concentration or disappearance of diphenylarsinic acid concomitantly with the culturing.

The steps of diluting the obtained culture fluid to prepare a dilution series; culturing the culture fluids of the dilution series in the presence of diphenylarsinic acid; and selecting, among the dilution series, a culture fluid exhibiting a decrease in concentration or disappearance of diphenylarsinic acid concomitantly with the culturing, can be repeatedly carried out a number of times, if desired. Furthermore, in a preferred embodiment, for the purpose of effective selection, the culturing in the presence of diphenylarsinic acid can be carried out by further adding an iron component such as ferrous sulfate. The collection of wet soil from arsenic-contaminated soil can be suitably carried out by collecting arsenic-contaminated paddy field soil.

According to such method for selecting a strain having an ability to degrade diphenylarsinic acid, it is possible to select (screening) and obtain such useful microorganisms as described above.

In addition, the inventors of the present invention discovered that the above-described strains of microorganism degrade phenylarsonic acid, which is a metabolic product of diphenylarsinic acid, and generates inorganic arsenic compounds.

Phenylarsonic acid is a kind of organoarsenic compound, and the strains of microorganism degrade diphenylarsinic acid to first generate phenylarsonic acid [$(C_6H_5)AsO(OH)_2$; the structural formula is shown as formula (II)]. However, for the purification of soil or underground water, it is preferable to further degrade and remove this phenylarsonic acid. If it is possible to degrade this phenylarsonic acid to inorganic arsenic compounds, the purification of soil or underground water may be achieved more thoroughly.

Formula II:

[Chemical Formula 2]

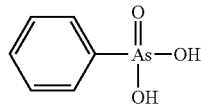

There, the present inventors further conducted investigations, and found that the above-described strains of microorganism degrade phenylarsonic acid which is a metabolic product of diphenylarsinic acid, and generates inorganic arsenic compounds.

That is, the present invention also provides the following [19] to [22].

[19] A method of degrading phenylarsonic acid by using the microorganism according to any one of [1] to [6].

[20] The method according to [19], wherein the microorganism is used in the presence of an iron component.

[21] A degradation agent of phenylarsonic acid, including the microorganism according to any one of [1] to [6].

[22] The degradation agent according to [21], including an iron component.

Furthermore, the present invention also provides the following [23] to [24].

[23] A method for producing an inorganic arsenic compound by degrading phenylarsonic acid using the microorganism according to any one of [1] to [6].

[24] The method according to [23], wherein the microorganism is used in the presence of an iron component.

The inventors of the present invention also discovered that the above-described strains of microorganism degrade roxarsone, which is used as a growth promoter for domestic fowls, and generates inorganic arsenic compounds.

Roxarsone [{$C_6H_3(NO_2)(OH)$}$AsO(OH)_2$; the structural formula is shown as formula (III)] is a phenylated organoarsenic compound which may be given to domestic fowls as a growth promoter. In the United States, the subject agent is given to about 70 percent of 8.3 billion broilers (as in year 2000), and the feedlot manure produced by the fowls contain 900 tons of roxarsone, which corresponds to 250 tons in terms of arsenic. In recent years, there are concerns about the generation of organoarsenic-contaminated soil as a result of applying this feedlot manure to agricultural fields and the like, and there is a demand for countermeasures to be taken against the contamination.

Formula III:

[Chemical Formula 3]

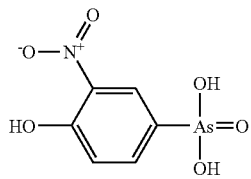

Thus, in order to clearly show the effect of the degrading bacteria isolated this time on roxarsone, the present inventors conducted an investigation on whether degradation of roxarsone in a medium is possible, by planting strain L2406 in an inorganic salt culture containing roxarsone as the only carbon source. As a result, the inventors discovered that the above-described strains of microorganism degrade roxarsone and generate inorganic arsenic compounds.

That is, the present invention also provides the following [25] to [28].

[25] A method for degrading roxarsone by using the microorganism according to any one of [1] to [6].

[26] The method according to [25], wherein the microorganism is used in the presence of an iron component.

[27] A degradation agent of roxarsone, including the microorganism according to any one of [1] to [6].

[28] The degradation agent according to [27], including an iron component.

Furthermore, the present invention also provides the following [29] to [30].

[29] A method for producing an inorganic arsenic compound by degrading roxarsone using the microorganism according to any one of [1] to [6].

[30] The method according to [29], wherein the microorganism is used in the presence of an iron component.

Effect of the Invention

The microorganisms having an ability to degrade diphenylarsinic acid of the present invention enable the degradation of diphenylarsinic acid, which is an organoarsenic compound detected in highest concentrations in certain types of arsenic contamination. Degradation agents of diphenylarsinic acid including these microorganisms provide a suitable method for degrading diphenylarsinic acid. Furthermore, when a method of purifying a soil or underground water contaminated with organoarsenic compounds is carried out by using such degradation agent of diphenylarsinic acid as a purifying agent for contaminated soil or contaminated underground water, excavation of contaminated soil or water abstraction, extraction of organic arsenic and the like are not required, enormous efforts and costs are not required, and purification can be achieved more conveniently in situ. In other words, the present invention makes it possible for the first time to apply bioremediation, which is one of new environment purifying technologies, to the removal of diphenylarsinic acid.

BRIEF DESCRIPTION OF THE DRAWINGS

FIG. 1 shows changes in the concentration of diphenylarsinic acid in the reflux liquid;

FIG. 2 shows changes in the concentration of diphenylarsinic acid in the medium in the L-shaped tube;

FIG. 3 shows changes in the concentration of diphenylarsinic acid in the medium in the conical flask;

FIG. 4 shows changes in the concentration of phenylarsonic acid in the culture fluid;

FIG. 5 shows the results for a morphological analysis (chromatogram) of arsenic in the culture fluid; and FIG. 6 shows changes in the concentration of roxarsone in the culture fluid.

BEST MODE FOR CARRYING OUT THE INVENTION

Hereinafter, the present invention will be described in detail.

The subject matters described in the specifications of Japanese Patent Application Nos. 2006-238350 and 2007-

115920, based on which the present patent application claims priority, are incorporated as part of the disclosure of the present specification.

The microorganisms having an ability to degrade diphenylarsinic acid of the present invention are bacteria separated from soil in the manner as described below.

Enrichment culture of diphenylarsinic acid degrading bacteria was carried out according to a soil/charcoal reflux method.

First, an autoclave-sterilized (120° C., 20 minutes) reflux liquid having the composition indicated in Table 1 was prepared. However, magnesium sulfate heptahydrate was separately prepared into a solution by itself at an appropriate concentration, and the solution was added to the reflux liquid after being separately sterilized in an autoclave.

[Table 1]

TABLE 1

Composition of reflux liquid

| Medium composition | Content |
| --- | --- |
| Ammonium nitrate | 0.5 g |
| Potassium dihydrogen phosphate | 0.5 g |
| Magnesium sulfate heptahydrate | 0.2 g |
| Ferrous sulfate heptahydrate | 5 mg (equivalent to 1 mg of iron) |
| Diphenylarsinic acid | 5 mg or 20 mg |
| Water | 1000 ml |

As for the source of microorganism, arsenic-contaminated paddy field soils I and II, which were collected from Kamisu city, Ibaraki Prefecture, were tested. These soils were respectively weighed while still wet, to an amount equivalent to 30 g of dry soil, and mixed with a small amount of charcoal (Charcoal A, manufactured by Toyo Denka Kogyo Co., Ltd.). The mixture was placed at a predetermined position inside a reflux apparatus. This apparatus was kept in a constant temperature chamber maintained at 25° C., and while refluxing 200 ml of the reflux liquid, enrichment of the degrading microorganism was carried out. Once in every two weeks, the reflux liquid was completely removed and replaced with a fresh reflux liquid having the same composition. The combinations of the soil under test and the concentration of diphenylarsinic acid in the reflux liquid for the reflux apparatuses operated this time, are summarized in Table 2.

[Table 2]

TABLE 2

Combination of soil under test and concentration of diphenylarsinic acid in reflux liquid

| Reflux apparatus | Soil under test | Diphenylarsinic acid concentration |
| --- | --- | --- |
| 1 | I | 20 mg/l |
| 2 | I | 20 mg/l |
| 3 | I | 5 mg/l |
| 4 | I | 5 mg/l |
| 5 | II | 20 mg/l |

During the enrichment culture, a very small amount of the reflux liquid was collected, and the concentration of diphenylarsinic acid was measured by high performance liquid chromatography (HPLC) under the measurement conditions indicated in Table 3. The results are shown in FIG. 1.

[Table 3]

TABLE 3

Conditions for measurement of diphenylarsinic acid concentration

| Item | Condition |
| --- | --- |
| Column | ODS Column, inner diameter 3 mm × length 250 mm |
| Mobile phase | Mixed liquid of water/acetonitrile (1:1) |
| Flow rate | 1 mg/min |
| Column temperature | 40° C. |
| Amount of sample injection | 10 µl |
| Detection | UV(220 nm) |
| Quantification | Absolute calibration method |

In FIG. 1, numerical references 1 to 5 respectively represent the number of the reflux apparatuses (see Table 2), and the ordinate indicates the relative values with respect to the initial diphenylarsinic acid concentration, while the arrows indicate the time points of replacement of the reflux liquid.

Nineteen days after commencing the reflux, soils were collected in an amount of 2 g, while still wet, respectively from the reflux apparatuses 3 and 4, which were considered to show a significant decrease in the concentration of diphenylarsinic acid in the reflux liquid and to be sufficiently enriched with the diphenyl arsenic acid degrading bacteria, among the reflux apparatuses operated this time. The soils were respectively dispersed in 20 ml of sterilized physiological saline to prepare soil suspensions. 0.1 ml each of these soil suspensions were inoculated respectively into 6 ml of sterilized liquid medium which had the same composition as that of the reflux liquid and was dispensed in L-shaped tubes, and the systems were subjected to shaking culture at 25° C. The concentration of diphenylarsinic acid at this time was set to 5 mg/l, and the current experiment was performed with four L-shaped tubes for each soil suspension, that is, 8 tubes in total. The diphenylarsinic acid concentration in the medium of each of the L-shaped tubes was measured over time by HPLC, and as a result, diphenylarsinic acid almost disappeared in all of the tubes after 9 days (see FIG. 2).

Then, the culture fluid of an arbitrarily selected L-shaped tube was diluted with sterilized physiological saline to prepare a dilution series, and 0.1 ml each of $10^4$-fold and $10^5$-fold dilutions were inoculated respectively into 6 ml of a sterilized liquid medium which had the same composition as that of the reflux liquid and had been dispensed in other L-shaped tubes. The systems were subjected to shaking culture at 25° C. Two cultures were provided for each of the dilutions in the series. The diphenylarsinic acid concentration in the medium of each of the L-shaped tubes was measured over time by HPLC, and after 17 days from the initiation of culture, diphenylarsinic acid almost disappeared in all of the L-shaped tubes (see FIG. 3).

Similarly, while the culture fluid of the L-shaped tube which had been inoculated with the $10^5$-fold dilution, was taken as the base, dilution and subculture were repeated so as to stabilize the microorganism species contained in the culture fluid, and then a portion thereof was seeded on a plate which was produced by adding 1.5% agar to DPAA20VTE medium having the composition indicated in Table 4. The plate was subjected to stationary culture at 30° C. After one week, colonies that appeared thereon were harvested and streaked on R2A agar medium (Difco), and the plate was further subjected to stationary culture at 30° C. to obtain a plurality of pure isolated strains. For these pure isolated strains, one platinum loop each thereof was inoculated into a conical flask having a capacity of 100 ml, into which 20 ml of DPAA5VTE medium (See Table 4) had been dispensed in advance, and the system was subjected to gyratory culture at 25° C. and 120 rpm. Then, the diphenylarsinic acid concentration in the medium was measured over time by HPLC, and thereby the selection of bacterial strains having an ability to degrade diphenylarsinic acid was carried out.

[Table 4]

TABLE 4

Composition of DPAA5VTE medium and composition of DPAA20VTE medium

| Medium composition | Content | |
| --- | --- | --- |
|  | DPAA5VTE medium | DPAA20VTE medium |
| Ammonium nitrate | 0.5 g | 0.5 g |
| Potassium dihydrogen phosphate | 0.5 g | 0.5 g |
| Magnesium sulfate heptahydrate | 0.2 g | 0.2 g |
| Ferrous sulfate heptahydrate | 5 mg (equivalent to 1 mg of iron) | 5 mg (equivalent to 1 mg of iron) |
| Diphenylarsinic acid | 5 mg | 20 mg |
| Vitamin solution ★1 | 10 ml | 10 ml |
| Trace element solution ★2 | 10 ml | 10 ml |
| Water | 1000 ml | 1000 ml |

[Table 5]

TABLE 5

★1 Composition of vitamin solution

| Constituent component | Content |
| --- | --- |
| Biotin | 10 mg |
| Cyanocobalamine | 20 mg |
| Calcium pantothenate | 25 mg |
| Thiamine | 50 mg |
| Nicotinic acid | 100 mg |
| Pyridoxine | 250 mg |
| p-Aminobenzoic acid | 500 mg |
| Water | 1000 ml |

[Table 6]

TABLE 6

★2 Composition of trace element solution

| Constituent component | Content |
| --- | --- |
| EDTA•2Na | 500 mg |
| $ZnSO_4•7H_2O$ | 10 mg |
| $MnSO_4•H_2O$ | 5 mg |
| $H_3BO_3$ | 30 mg |
| $CoSO_4•7H_2O$ | 24 mg |
| $CuSO_4•5H_2O$ | 5 mg |
| $Na_2MoO_4•2H_2O$ | 5 mg |
| $Ca(OH)_2$ | 50 mg |
| Water | 1000 ml |

Through the above-discussed operations, the selection of bacterial strains having an ability to degrade diphenylarsinic acid was carried out, and it was found that strain L2406 and strain L2413 have the ability to degrade diphenylarsinic acid. For each of the strains, single colonies were separated again in R2A agar medium (Difco), and five strains each were inoculated into L-shaped tubes in which 6 ml each of DPAA5VTE medium had been dispensed. These were subjected to shaking culture for 14 days at 25° C., and the amount of remnant diphenylarsinic acid was measured by HPLC, while the amount of produced phenylarsonic acid, which is a metabolic product, was measured by LC-MS. The results are presented in Table 7. In addition, the analytical conditions for LC-MS were as indicated in Table 8.

[Table 7]

TABLE 7

Degradation of diphenylarsinic acid and production of metabolic product by strain L2406 and strain L2413

| Strain under test | Colony No. | Rate of degradation of diphenylarsinic acid (%) | Amount of production of phenylarsonic acid (mg/l) |
| --- | --- | --- | --- |
| Strain L2406 | 1 | 39.4 | 0.52 |
|  | 2 | 38.9 | 0.48 |
|  | 3 | 37.1 | 0.44 |
|  | 4 | 34.4 | 0.46 |
|  | 5 | 36.4 | 0.43 |
| Strain L2413 | 1 | 22.6 | 0.27 |
|  | 2 | 12.2 | 0.17 |
|  | 3 | 14.8 | 0.20 |
|  | 4 | 13.4 | 0.19 |
|  | 5 | 17.2 | 0.22 |

[Table 8]

TABLE 8

Conditions for LC-MS

| Item | Condition |
| --- | --- |
| Conditions for separation | Same as in Table 2 |
| Method of ionization | Electrospray method |
| Mode | Positive |
| Gain | 1.0 |
| Drying gas | Nitrogen (12 ml/min, 350° C.) |
| Nebulizer pressure | 45 psig |
| Capillary voltage | 3.5 kV |
| Fragmentor voltage | 80 eV |
| Quantification | Absolute calibration method |

For the strain L2406 and strain L2413 discovered by the procedure as described above, a genetic taxonomic investigation was conducted on the basis of the base sequence of 16S ribosomal RNA gene (16S ribosome RNA gene). First, each bacterial strain was inoculated into R2A agar medium (Difco), and was pre-cultured in a dark room at 30° C. One platinum loop of the produced colonies was dispersed in 1 ml of sterilized physiological saline, and DNA was extracted therefrom using a DNeasy Tissue Kit (Qiagen). PCR was performed using the obtained DNA as a template, and using conventionally known D1f (SEQ ID NO: 3) and D1r (SEQ ID NO: 4) as primers, to thus amplify the 16S ribosomal RNA gene. This PCR product was purified with a QIAquick PCR Purification Kit (Qiagen), and then was submitted to a cycle sequencing reaction. The reaction product was analyzed by a DNA sequencer (SQ-5500E manufactured by Hitachi, Ltd.), to determine the base sequence. As a result, 1101 base pairs (SEQ ID NO: 1) were determined for the strain L2406, while 1276 base pairs (SEQ ID NO: 2) were determined for the strain L2413.

Based on the determined base sequences, a FASTA search was conducted against the DNA base sequence database (GenBank) using GENETYX PDB, and as a result, the strain L2406 was found to have a homology of 99.5% with Sinorhizobium morelense, while the strain L2413 was found to have a homology of 99.5% with Ensifer adhaerens.

In the following, the results of conducting an investigation on the morphological and physiological properties of strain L2406 and strain L2413 are presented in Table 9. The mark "+" in Table 9 represents presence or positiveness, while the mark "−" represents absence or negativeness.

[Table 9]

TABLE 9

Morphological and physiological properties of strain L2406 and strain L2413

| Test item | | Strain L2406 | Strain L2413 |
|---|---|---|---|
| Shape | | *Bacillus* (0.7~0.8 × 1.5~2.0 μm) | *Bacillus* (0.7~0.8 × 1.5~2.0 μm) |
| Gram staining | | − | − |
| Sporulation | | − | − |
| Mobility | | + | + |
| Morphology of colony (after 24 hours) | | Medium for observation: nutrient agar (temperature of culture: 30° C.) Diameter: 1.0 mm Color: cream color Form: round form State of protuberance: lens shape Margin: entire margin Surface shape, etc.: smooth Transparency: opaque Consistency: butter-like (for L2406) | Medium for observation: nutrient agar (temperature of culture: 30° C.) Diameter: 1.0 mm Color: cream color Form: round form State of protuberance: lens shape Margin: entire margin Surface shape, etc.: smooth Transparency: opaque Consistency: viscid (for L2413) |
| Culturing temperature | 37° C. | + | + |
| | 45° C. | − | − |
| Catalase | | + | + |
| Oxidase | | + | + |
| Acid/gas production | | −/− | −/− |
| O/F test | | +/− | +/− |
| Anaerobic growth | | − | − |
| Growth in medium | 4% | − | − |
| | 2% | + | + |

(+: presence or positive, −: absence or negative)

Furthermore, the results of conducting an investigation on the biochemical nature of the two strains according to the measurement method of API20NE of the API System (Biomerieux Corp.), are presented in Table 10.

[Table 10]

TABLE 10

Biochemical nature of strain L2406 and strain L2413

| Test item | Strain L2406 | Strain L2413 |
|---|---|---|
| Biochemical tests | | |
| Nitrate reduction | + | + |
| Indole production | − | − |
| Glucose acidification | − | − |
| Arginine dihydrolase | − | − |
| Urease | − | + |
| Esculin hydrolysis | + | + |
| Gelatin hydrolysis | − | − |
| β-Galactosidase | + | + |
| Cytochrome oxidase | + | + |
| Fermentability tests | | |
| Glucose | + | + |
| L-arabinose | + | + |
| D-mannose | + | + |
| D-mannitol | + | + |
| N-acetyl-D-glucosamine | + | + |
| Maltose | + | + |
| Potassium gluconate | − | − |
| n-capric acid | − | − |
| Adipic acid | − | − |
| dl-malic acid | + | + |
| Sodium citrate | − | − |
| Phenyl acetate | − | − |

The results shown above did not contradict the features of the bacteria of genus *Sinorhizobium* and the bacteria of genus *Ensifer* described in "Brenner, D. J., Krieg, N. R., Staley, J. T., Garrity, G. M., co-authors. Bergey's Manual of Systematic Bacteriology, $2^{nd}$ Ed., The Proteobacteria."

From the results shown above, the inventors identified the strain L2406 as *Sinorhizobium* sp. L2406, and deposited the strain with the International Patent Organism Depositary, National Institute of Advanced Industrial Science and Technology, under Accession No. FERM BP-10658. The inventors also identified the strain L2413 as *Ensifer* sp. L2413, and deposited the strain with the International Patent Organism Depositary, National Institute of Advanced Industrial Science and Technology, under Accession No. FERM BP-10659.

The DPAA5VTE medium used in the isolation of strain L2406 and strain L2413 contains, as trace elements, iron, zinc, manganese, boron, cobalt, copper, molybdenum and calcium. The necessity of these elements in the degradation of diphenylarsinic acid by the two strains was tested, and it was found that the addition of iron is very important. Thus, DPAA5VTE media were prepared such that the iron concentrations in the media were set to 0, 0.04, 0.2, 0.4, 1, 2 and 4 mg-Fe/l by varying the amount of ferrous sulfate heptahydrate being added, and an investigation was conducted on what influence the iron concentration in the medium would exert on the ability to degrade of the diphenylarsinic acid degrading bacteria.

Each of the media was dispensed in an L-shaped tube in an amount of 6 ml, and the strain L2406 or the strain L2413 was inoculated into the medium. The system was subjected to shaking culture for 7 days at 25° C., and then the diphenylarsinic acid concentration in the culture fluid was measured by HPLC, to thereby determine the rate of degradation. As a result, the degradation of diphenylarsinic acid by strain L2406 and strain L2413 was accelerated, as the iron concentration in the medium increased (Table 11).

[Table 11]

TABLE 11

Iron concentration dependency of diphenylarsinic acid degradation

| Strain under test | Iron concentration (mg-Fe/l) | Rate of degradation of diphenylarsinic acid (%) |
|---|---|---|
| L2406 | 0 | 1.5 |
| | 0.04 | 4.2 |
| | 0.2 | 18.8 |
| | 0.4 | 35.4 |
| | 1 | 35.2 |
| | 2 | 32.0 |
| | 4 | 35.5 |
| L2413 | 0 | 0.3 |
| | 0.04 | 1.7 |

TABLE 11-continued

Iron concentration dependency of diphenylarsinic acid degradation

| Strain under test | Iron concentration (mg-Fe/l) | Rate of degradation of diphenylarsinic acid (%) |
|---|---|---|
| | 0.2 | 7.1 |
| | 0.4 | 14.8 |
| | 1 | 10.6 |
| | 2 | 13.3 |
| | 4 | 17.3 |

EXAMPLES

The following examples are illustrative of the present invention and should not be construed as limiting the scope of the invention in any manner.

[Enrichment Culture of Diphenylarsinic Acid Degrading Bacteria]

The enrichment culture of diphenylarsinic acid degrading bacteria was carried out by a soil/charcoal reflux method. First, an autoclave-sterilized (120° C., 20 minutes) reflux liquid having the composition indicated in Table 1 was prepared. However, magnesium sulfate heptahydrate was separately prepared into a solution by itself at an appropriate concentration, and the solution was added to the reflux liquid after being separately sterilized in an autoclave.

As the source of microorganism, arsenic-contaminated paddy field soils I and II, which were collected from Kamisu city, Ibaraki Prefecture, were tested. These soils were respectively weighed while still wet, to an amount equivalent to 30 g of dry soil, and mixed with a small amount of charcoal (Charcoal A, manufactured by Toyo Denka Kogyo Co., Ltd.). The mixture was placed at a predetermined position inside a reflux apparatus. This apparatus was kept in a constant temperature chamber maintained at 25° C., and while refluxing 20 ml of the reflux liquid, enrichment of the degrading microorganism was carried out. Once in every two weeks, the reflux liquid was completely removed and replaced with a fresh reflux liquid having the same composition. The combinations of the soil under test and the concentration of diphenylarsinic acid in the reflux liquid for the reflux apparatuses operated this time, are summarized in Table 2.

[Measurement of Concentration of Diphenylarsinic Acid]

During the enrichment culture, a very small amount of the reflux liquid was collected, and the concentration of diphenylarsinic acid was measured by high performance liquid chromatography (HPLC) under the measurement conditions indicated in Table 3. The results are shown in FIG. 1.

Nineteen days after commencing the reflux, soils were collected in an amount of 2 g, while still wet, respectively from the reflux apparatuses 3 and 4, which were considered to show a significant decrease in the concentration of diphenylarsinic acid in the reflux liquid and to be sufficiently enriched with the diphenyl arsenic acid degrading bacteria, among the reflux apparatuses operated this time. The soils were respectively dispersed in 20 ml of sterilized physiological saline to prepare soil suspensions. 0.1 ml each of these soil suspensions were inoculated respectively into 6 ml of sterilized liquid medium which had the same composition as that of the reflux liquid and was dispensed in L-shaped tubes, and the systems were subjected to shaking culture at 25° C. The concentration of diphenylarsinic acid at this time was set to 5 mg/l, and the current experiment was performed with four L-shaped tubes for each soil suspension, that is, 8 tubes in total. The diphenylarsinic acid concentration in the medium of each of the L-shaped tubes was measured over time by HPLC, and as a result, diphenylarsinic acid almost disappeared in all of the tubes after 9 days (see FIG. 2).

[Preparation of Dilution Series and Selection of Culture Fluid]

The culture fluid of an arbitrarily selected L-shaped tube was diluted with sterilized physiological saline to prepare a dilution series, and 0.1 ml each of $10^4$-fold and $10^5$-fold dilutions were inoculated respectively into 6 ml of a sterilized liquid medium which had the same composition as that of the reflux liquid and had been dispensed in other L-shaped tubes. The systems were subjected to shaking culture at 25° C. Two cultures were provided for each of the dilutions in the series. The diphenylarsinic acid concentration in the medium of each of the L-shaped tubes was measured over time by HPLC, and after 17 days from the initiation of culture, diphenylarsinic acid almost disappeared in all of the L-shaped tubes (see FIG. 3).

Similarly, while the culture fluid of the L-shaped tube which had been inoculated with the $10^5$-fold dilution, was taken as the base, dilution and subculture were repeated so as to stabilize the microorganism species contained in the culture fluid, and then a portion thereof was seeded on a plate which was produced by adding 1.5% agar to DPAA20VTE medium having the composition indicated in Table 4. The plate was subjected to stationary culture at 30° C. After one week, emerging colonies were caught and streaked on R2A agar medium (Difco), and the plate was further subjected to stationary culture to obtain a plurality of pure isolated strains at 30° C. For these pure isolated strains, one platinum loop each thereof was inoculated into a conical flask having a capacity of 100 ml, into which 20 ml of DPAA5VTE medium had been dispensed in advance, and the system was subjected to gyratory culture at 25° C. and 120 rpm. Then, the diphenylarsinic acid concentration in the medium was measured over time by HPLC, and thereby the selection of bacterial strains having an ability to degrade diphenylarsinic acid was carried out.

[Selection and Characterization of Bacterial Strains]

Through the above-discussed operations, the selection of bacterial strains having an ability to degrade diphenylarsinic acid was carried out, and it was found that strain L2406 and strain L2413 have the ability to degrade diphenylarsinic acid. For each of the strains, single colonies were separated again in R2A agar medium (Difco), and five strains each were inoculated into L-shaped tubes in which 6 ml each of DPAA5VTE medium had been dispensed. These were subjected to shaking culture for 14 days at 25° C., and the amount of remnant diphenylarsinic acid was measured by HPLC, while the amount of produced phenylarsonic acid, which is a metabolic product, was measured by LC-MS. The results are presented in Table 7. In addition, the analytical conditions for LC-MS were as indicated in Table 8.

[Characterization and Deposition of Bacterial Strains]

For the strain L2406 and strain L2413 discovered by the procedure as described above, a genetic taxonomic investigation was conducted on the basis of the base sequence of 16S ribosomal RNA gene. First, each bacterial strain was inoculated into R2A agar medium (Difco), and was pre-cultured in a dark room at 30° C. One platinum loop of the produced colonies was dispersed in 1 ml of sterilized physiological saline, and DNA was extracted therefrom using a DNeasy Tissue Kit (Qiagen). PCR was performed using the obtained DNA as a template, and using conventionally known D1f (SEQ ID NO: 3) and D1r (SEQ ID NO: 4) as primers, to thus amplify the 16S ribosomal RNA gene. This PCR product was purified with a QIAquick PCR Purification Kit (Qiagen), and then was submitted to a cycle sequencing reaction. The reaction product was analyzed by a DNA sequencer (SQ-5500E manufactured by Hitachi, Ltd.), to determine the base sequence. As a result, 1101 base pairs (SEQ ID NO: 1) were determined for the strain L2406, while 1276 base pairs (SEQ ID NO:2) were determined for the strain L2413.

Based on the determined base sequences, a FASTA search was conducted against the DNA base sequence database (GenBank) using GENETYX PDB, and as a result, the strain L2406 was found to have a homology of 99.5% with *Sinorhizobium morelense*, while the strain L2413 was found to have a homology of 99.5% with *Ensifer adhaerens*.

In the following, the results of conducting an investigation on the morphological and physiological properties of strain L2406 and strain L2413 are presented in Table 9. The mark "+" in Table 9 represents presence or positiveness, while the mark "−" represents absence or negativeness.

Furthermore, the results of conducting an investigation on the biochemical nature of the two strains according to the measurement method of API20NE of the API System (Biomerieux Corp.), are presented in Table 10.

The results shown above did not contradict the features of the bacteria of genus *Sinorhizobium* and the bacteria of genus *Ensifer* described in "Brenner, D. J., Krieg, N. R., Staley, J. T., Garrity, G. M., co-authors. Bergey's Manual of Systematic Bacteriology, $2^{nd}$ Ed., The Proteobacteria."

From the results shown above, the inventors identified the strain L2406 as *Sinorhizobium* sp. L2406, and deposited the strain with the International Patent Organism Depositary, National Institute of Advanced Industrial Science and Technology, under Accession No. FERM BP-10658. The inventors also identified the strain L2413 as *Ensifer* sp. L2413, and deposited the strain with the International Patent Organism Depositary, National Institute of Advanced Industrial Science and Technology, under Accession No. FERM BP-10659.

[Investigation of Conditions for Degradation of Diphenylarsinic Acid]

The DPAA5VTE medium used in the isolation of strain L2406 and strain L2413 contains, as trace elements, iron, zinc, manganese, boron, cobalt, copper, molybdenum and calcium. The necessity of these elements in the degradation of diphenylarsinic acid by the two strains was tested, and it was found that the addition of iron is very important. Thus, DPAA5VTE media were prepared such that the iron concentrations in the media were set to 0, 0.04, 0.2, 0.4, 1, 2 and 4 mg-Fe/l by varying the amount of ferrous sulfate heptahydrate being added, and an investigation was conducted on what influence the iron concentration in the medium would exert on the ability to degrade of the diphenylarsinic acid degrading bacteria.

Each of the media was dispensed in an L-shaped tube in an amount of 6 ml, and the strain L2406 or the strain L2413 was inoculated into the medium. The system was subjected to shaking culture for 7 days at 25° C., and then the diphenylarsinic acid concentration in the culture fluid was measured by HPLC, to thereby determine the rate of degradation. As a result, the degradation of diphenylarsinic acid by strain L2406 and strain L2413 was accelerated, as the iron concentration in the medium increased (Table 11).

[Investigation on Degradation of Phenylarsonic Acid]

As presented in Table 7, the strain L2406 and strain L2413 degrade diphenylarsinic acid and generate phenylarsonic acid [$(C_6H_5)AsO(OH)_2$; the structural formula is shown as formula II]. However, for all of the strains, the amount of detected phenylarsonic acid was merely about one-third of the amount of degraded diphenylarsinic acid in terms of arsenic, and from this result, it was conceived that there is a possibility that these strains would further degrade phenylarsonic acid. Thus, in the next step, the diphenylarsinic acid degrading bacteria were inoculated into an inorganic salt medium containing phenylarsonic acid as the only carbon source, and the amount of phenylarsonic acid in the medium was measured over time.

First, strain L2406 was pre-cultured in R2A agar medium (Difco) (the composition is indicated in Table 12), and the colonies generated therefrom were scraped off and suspended in sterilized physiological saline. Next, a medium prepared by excluding diphenylarsinic acid from the DPAA5VTE medium shown in Table 4, and adding 1 mg of phenylarsonic acid instead of diphenylarsinic acid, was designated as PAA1VTE medium, and 20 ml of the PAA1VTE medium was placed in a conical flask having a capacity of 100 ml. To each of such conical flasks, the bacterial cell suspension of strain L2406 previously prepared was inoculated in an amount of 0.1 ml each, and the bacterial cells were subjected to gyratory culture (120 rpm) in a dark room at 30° C. A conical flask which was not inoculated was also provided to be used as control. The current test was performed with n=2, and LC-MS was used in the quantification of phenylarsonic acid in the medium, while the analytical conditions shown in Table 8 were applied.

The results are shown in FIG. 4. The open circle (○) in FIG. 4 represents the average value of changes over time in the phenylarsonic acid concentration in the culture fluid when the strain L2406 was inoculated. The ordinate in FIG. 4 indicates the relative values of the phenylarsonic acid concentration in the culture fluid with respect to the phenylarsonic acid concentration in the control, while the abscissa indicates the number of culturing days. As is clear from FIG. 4, the strain L2406 has an ability to decrease the phenylarsonic acid concentration in an inorganic salt medium which contains phenylarsonic acid as the only carbon source.

Furthermore, a morphological analysis of arsenic was conducted for the culture fluids after 14 days, using LC-ICP/MS. The separation conditions at the time of the analysis by LC-ICP/MS are as shown in Table 13.

[Table 12]

TABLE 12

| Composition of R2A agar medium (final pH: 7.2 ± 0.2) | |
|---|---|
| Composition of medium | Content |
| Yeast extract | 0.5 g |
| Proteose peptone (Difco No. 3) | 0.5 g |
| Casamino acid | 0.5 g |
| Glucose | 0.5 g |
| Soluble starch | 0.5 g |
| Dipotassium monohydrogen phosphate | 0.3 g |
| Magnesium sulfate heptahydrate | 0.05 g |
| Sodium pyruvate | 0.3 g |
| Agar | 15.0 g |
| Water | 1000 ml |

TABLE 13

| Item | Conditions |
|---|---|
| Column | ODS column, inner diameter 2 mm × length 150 mm |
| Mobile phase | Liquid A, 0.1% formic acid |
| | Liquid B, 0.1% formic acid-containing methanol |
| Gradient condition | After injection, the mixing proportion of liquid B is maintained at 1% until 1.5 minutes. |

TABLE 13-continued

| Item | Conditions |
| --- | --- |
|  | During the period from 1.5 minutes past to 4 minutes past, the mixing proportion of the liquid B is linearly increased to 25%. During the period from 4 minutes past to 11 minutes past, the mixing proportion of the liquid B is maintained at 25%. During the period from 11 minutes past to 15 minutes past, the mixing proportion of the liquid B is linearly increased to 75%. During the period from 15 minutes past to 20 minutes past, the mixing proportion of the liquid B is maintained at 75%. |
| Flow rate | 0.15 ml/min |
| Column temperature | 40° C. |

The chromatogram obtained by LC-ICP/MS is shown in FIG. 5. The ordinate indicates the peak intensity, while the abscissa indicates the elution time. The upper diagram shows the chromatogram of a standard sample, in which AsIII refers to the position of peak elution of arsenious acid, DMAA+ MAA to that of dimethylarsinic acid and monomethylarsonic acid, AsV to that of arsenic acid, DMPAO to that of dimethylphenylarsine oxide, MPAA to that of methylphenylarsinic acid, PAA to that of phenylarsonic acid, MDPAO to that of methyldiphenylarsine oxide, and DPAA to that of diphenylarsinic acid (20 mg/l respectively). The lower diagram shows the chromatogram of a culture fluid of the strain L2406 obtained by culturing for 28 days, and peaks corresponding to arsenious acid (peak of (1) in the lower diagram of FIG. 5) and to arsenic acid (peak of (2) in the lower diagram of FIG. 5) were detected. Furthermore, three kinds of arsenic compounds that are unknown were also detected (peak of (3) in the lower diagram of FIG. 5). Residual phenylarsonic acid which was not degraded was detected at the position of (4) in the lower diagram of FIG. 5. On the other hand, in the control (no inoculation), only the peak for phenylarsonic acid appeared. From the results discussed above, it could be concluded that the strain L2406 has an ability to degrade phenylarsonic acid and generate inorganic arsenic.

As the microorganisms which degrade phenylarsonic acid and generate inorganic arsenic, strain K-1' and strain IV-1 have been reported (Patent Document 6). However, the rates of degradation of phenylarsonic acid (%) of those microorganisms are very slow, such that in a culture of two weeks, the rate of the strain K-1' is 0.63%, and that of the strain IV-1 is 2.20%. On the contrary, in the case of strain L2406, the rate of degradation in two weeks is about 10%, and even reaches 40% in four weeks, and thus it was concluded that the applicability of the strain to bioremediation is higher.

[Investigation on Degradation of Roxarsone]

Roxarsone [{$C_6H_3(NO_2)$ (OH)}$AsO(OH)_2$; the structural formula is shown in formula (III)] is a phenylated organoarsenic compound which can be given to domestic fowls as a growth promoter. In the United States, the subject agent is given to about 70 percent of 8.3 billion broilers (as in year 2000), and the feedlot manure produced by the fowls contain 900 tons of roxarsone, which corresponds to 250 tons in terms of arsenic. In recent years, there are concerns about the generation of organoarsenic-contaminated soil as a result of applying this feedlot manure to agricultural fields and the like, and there is a demand for countermeasures to be taken against the contamination. Therefore, in the current study, in order to elucidate the effect of the degrading bacteria isolated this time on roxarsone, an investigation was conducted to see if the degradation of roxarsone in a medium is possible, by inoculating the strain L2406 into an inorganic salt medium containing roxarsone as the only carbon source.

First, strain L2406 was pre-cultured in R2A agar medium (Difco), and the colonies generated therefrom were scraped off and suspended in sterilized physiological saline. Next, a medium prepared by excluding diphenylarsinic acid from the DPAA5VTE medium shown in Table 4, and adding 6 mg of roxarsone instead of diphenylarsinic acid, was designated as ROX6VTE medium, and 20 ml of the ROX6VTE medium was placed in a conical flask having a capacity of 100 ml. To each of such conical flasks, the bacterial cell suspension of strain L2406 previously prepared was inoculated in an amount of 0.1 ml each, and the bacterial cells were subjected to gyratory culture (120 rpm) in a dark room at 30° C. A conical flask which was not inoculated was also provided to be used as control. The current test was performed with n=2, and HPLC was used in the quantification of roxarsone in the medium, while the analytical conditions shown in Table 13 were applied.

The results are presented in FIG. 6. The solid lozenge (♦) in FIG. 6 represents the average value of changes over time in the roxarsone concentration in the culture fluid when the strain L2406 was inoculated. The ordinate in FIG. 6 indicates the relative values of the roxarsone concentration in the culture fluid with respect to the roxarsone concentration in the control, while the abscissa indicates the number of culturing days. As is clear from FIG. 6, the strain L2406 has an ability to decrease the roxarsone concentration in an inorganic salt medium which contains roxarsone as the only carbon source.

INDUSTRIAL APPLICABILITY

The microorganisms having an ability to degrade diphenylarsinic acid of the present invention enable the degradation of diphenylarsinic acid, which is an organoarsenic compound detected in highest concentrations in certain types of arsenic contamination. Degradation agents of diphenylarsinic acid containing these microorganisms provide a suitable method for degrading diphenylarsinic acid. When a method of purifying a soil or underground water contaminated with organoarsenic compounds is carried out by using such degradation agent of diphenylarsinic acid as a purifying agent for contaminated soil or contaminated underground water, excavation of contaminated soil or water abstraction, extraction of organic arsenic and the like are not required, enormous efforts and costs are not required, and purification can be achieved more conveniently in situ. In other words, the present invention makes it possible for the first time to apply bioremediation, which is one of new environment purifying technologies, to the removal of diphenylarsinic acid.

Therefore, the present invention is to provide a new excellent environment purifying technology, which is industrially useful.

Free Text of Sequence List

SEQ ID NO:1: 1101 bases of 16S ribosomal RNA gene of strain L2406, the degrading bacterium of the present invention.

SEQ ID NO:2: 1276 bases of 16S ribosomal RNA gene of strain L2413, the degrading bacterium of the present invention.

The invention claimed is:

1. An isolated microorganism, which is Strain L2406 deposited under FERM BP-10658 having an ability to degrade diphenylarsinic acid and belonging to genus *Sinorhizobium*.

2. A method for degrading diphenylarsinic acid, the method comprising:
   contacting the microorganism according to claim 1 with soil or contaminated underground water to degrade diphenylarsinic acid which is contained in the soil or contaminated underground water.

3. The method according to claim 2, wherein said contacting is contacting the microorganism with the soil or contaminated underground water in the presence of an iron component.

4. A degradation agent of diphenylarsinic acid, wherein the degradation agent is a composition comprising the isolated microorganism according to claim 1.

5. The degradation agent according to claim 4, wherein the composition further comprises an iron component.

6. A purifying agent for contaminated soil and/or contaminated underground water, wherein the purifying agent is a composition comprising the isolated microorganism according to claim 1.

7. The purifying agent according to claim 6, comprising wherein the composition further comprises an iron component.

8. A method for degrading phenylarsonic acid, the method comprising:
   contacting the microorganism according to claim 1 with soil or contaminated underground water to degrade phenylarsonic acid which is contained in the soil or contaminated underground water.

9. A method for degrading roxarsone, the method comprising:
   contacting the microorganism according to claim 1 with soil or contaminated underground water to degrade roxarsone which is contained in the soil or contaminated underground water.

10. The method according to claim 8, wherein said contacting is contacting the microorganism with the soil or contaminated underground water in the presence of an iron component.

11. A degradation agent of phenylarsonic acid, wherein the degradation agent is a composition comprising the microorganism according to claim 1.

12. A degradation agent of roxarsone, wherein the degradation agent is a composition comprising the microorganism according to claim 1.

13. The degradation agent according to claim 11, wherein the composition further comprises an iron component.

14. The method according to claim 9, wherein said contacting is contacting the microorganism with the soil or contaminated underground water in the presence of an iron component.

15. The degradation agent according to claim 12, wherein the composition further comprises an iron component.

\* \* \* \* \*